United States Patent [19]

Powell

[11] 4,006,156
[45] Feb. 1, 1977

[54] 3-ALKYL-2-(NITROMETHYLENE) THIAZOLIDINE

[75] Inventor: James E. Powell, Modesto, Calif.
[73] Assignee: Shell Oil Company, Houston, Tex.
[22] Filed: June 27, 1975
[21] Appl. No.: 590,984
[52] U.S. Cl. .................. 260/306.7 R; 424/246
[51] Int. Cl.$^2$ .................. C07D 277/10
[58] Field of Search .................. 260/306.7 R
[56] References Cited
UNITED STATES PATENTS 2,815,338  12/1957  Ruegg .................. 260/306.7 R
3,624,217  11/1971  Koch .................. 260/306.7 R

OTHER PUBLICATIONS

Feuer et al., "J. Org. Chem" vol. 37, No. 23, pp. 3662–3670 (1972).
Lawrence, PhD thesis, Purdue University, June, 1970.

Primary Examiner—Donald G. Daus
Assistant Examiner—David E. Wheeler

[57] ABSTRACT

Novel insecticidal 3-alkyl-2-(nitromethylene)-thiazolidines.

2 Claims, No Drawings

3-ALKYL-2-(NITROMETHYLENE) THIAZOLIDINE

DESCRIPTION OF THE INVENTION

It has been found that useful insecticidal activity is possessed by certain 3-alkyl-2-(nitromethylene)-thiazolidines described by the formula:

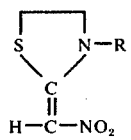

wherein R represents alkyl of from 1 to three carbon atoms.

The compounds of this invention are resonance hybrids and may exist as geometric (cis-trans) isomers, depending upon the spatial relationship of the moieties about the bond between the carbon atom of the nitromethylene moiety and the ring carbon atom to which it is joined. In this specification, for the sake of simplicity, these compounds are defined in terms of formula (I). The definition is intended to include all of the contributors of the resonance hybrid and the geometric isomers, as well as mixtures thereof.

The compounds of this invention can be prepared by treating nitroketene dimethyl mercaptole (R. Gompper and H. Schaefer, Berichte, 100, 591 (1967)) with a 2-(R-amino)-1-mercaptoethane (D. S. Tarbell and D. P. Cameron, J. Am. Chem. Soc., 78, 2731-5 (1956)), by mixing the reactants in a suitable liquid medium such as a lower alkanol. The reaction can in some cases be carried out at essentially room temperature, whereas in other cases gentle to moderate heating (up to 100° C) may be required. Generally, it will be found best to employ a slight to moderate excess (5-25%) of the thiol over that theoretically required to react with the mercaptole. For best results, oxygen should be excluded from the reaction zone by conducting the reaction in a nitrogen atmosphere. The product can be recovered by removing the solvent, digesting the residue with water and then extracting the desired product from the aqueous phase by means of a suitable solvent such as methylene chloride.

The procedures for preparing compounds of this invention are illustrated in the following example of the preparation of a particular species of such compounds. The identity of the precursor(s) was established and the identity of the final product was confirmed, by elemental analysis and by infrared and nuclear magnetic resonance spectrum analyses:

EXAMPLE 1

3-methyl-2-(nitromethylene)thiazolidine (1)

12.4 g of nitroketene dimethyl mercaptole was added over a period of about one minute to a solution of 2-methylamino)-1-mercaptoethane in 150 ml of ethanol at room temperature. The mixture was refluxed for 1 hour, then stored in a refrigerator overnight. The cold mixture was filtered and the filtrate was heated to boiling with activated charcoal. After filtration, the solvent was evaporated under reduced pressure. The resulting dark oil was chromatographed on Florosil, using the solvent sequence: (a) chloroform; (b) 9:1 chloroform/methanol; (c) 3:1 chloroform/methanol; (d) 3:2 chloroform/methanol; (e) 2:3 chloroform/methanol. The portion that was eluted by solvent (b) was dissolved in hot methanol and treated with charcoal. Filtration and evaporation gave a brown gummy solid that was dissolved in hot ethyl acetate. Cooling the solution gave a brown solid that was recrystallized from chloroform to give 1 as a beige solid, m.p.: 169°-171°. Further 1 was obtained from the mother liquor from the recrystallization.

The compounds of this invention exhibit useful insecticidal activity, being of particular interest for control of the larval "caterpillar" or "worm" forms of insects of the genus Heliothis, such as $H.$ $zea$ (corn earworm, cotton bollworm, tomato fruitworm), $H.$ $virescens$ (tobacco budworm); the genus $Agrotis$, such as $A.$ $ipsilon$ (black cutworm); the genus $Trichoplusia$, such as $T.$ $ni$ (cabbage looper), and the genus Spodoptera, such as $S.$ $littoralis$ (Egyptian cotton leafworm).

The activity of compound 1 with respect to insects was determined by using standardized test methods to establish the $LC_{50}$ dosage (in milligrams of test compound per 100 milliliters of solvent or liquid carrier required in the solution of suspension of test compound used) that was required to kill 50% of the test insects. The test insects were the housefly, corn earworm, mosquito, pea aphid and 2-spotted spider mite.

Compound 1 was found to be quite toxic with respect to the corn earworms, moderately toxic with respect to the aphids, and not toxic to the other species of insects. It was found that it affected the corn earworms and aphids very rapidly.

The invention includes within its scope insecticidal compositions comprising an adjuvant — that is, a carrier, optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin with which the active compound is mixed or formulated to facilitate its application to the plant, seed, soil or other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natrual and synthetic resins such as for example, coumarone resins, polyvinyl chloride and styrene polymers and copolymers, solid polychlorophenols; bitumen; waxes such as beeswax, paraffin wax and chlorinated mineral waxes; degradable organic solids such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers; aromatic hydrocarbons, such as benzene, toluene and xylene; petroleum fractions, such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkyaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3-10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½-10%w of toxicant. Granules may be manufactured by agglomeration or impregnation techniques. Generally, granules will contain ½25%w toxicant and 0–10%w of additives such as stabilizers, slow release modifiers and binding agents.

Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0-10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e., the dosage to which the insect contacts — is of the order of 0.001% to 0.5% based on the total weight of the formulation, through under some circumstances the effective concentration will be as little as 0.0001% or as much as 2%, on the same basis.

What is claimed is:
1. A 3-alkyl-2-(nitromethylene)thiazolidine in which the alkyl moiety has from 1 to 3 carbon atoms.
2. A compound of claim 1 wherein the alkyl moiety is methyl.

* * * * *